United States Patent [19]
Lorenzo

[11] Patent Number: 6,056,702
[45] Date of Patent: May 2, 2000

[54] GUIDEWIRE WITH OUTER SHEATH

[75] Inventor: Juan A. Lorenzo, Ft. Lauderdale, Fla.

[73] Assignee: Cordis Corporation, Miami, Fla.

[21] Appl. No.: 09/165,517

[22] Filed: Oct. 2, 1998

[51] Int. Cl.$^7$ ...................................................... A61B 5/00
[52] U.S. Cl. ............................................................. 600/585
[58] Field of Search ..................................... 600/434, 585; 604/280–283

[56] References Cited

U.S. PATENT DOCUMENTS

| | | |
|---|---|---|
| Re. 34,695 | 8/1994 | Mar et al. . |
| 3,749,086 | 7/1973 | Kline et al. . |
| 4,044,765 | 8/1977 | Kline . |
| 4,456,017 | 6/1984 | Miles . |
| 4,773,432 | 9/1988 | Rydell . |
| 4,798,598 | 1/1989 | Bonello et al. . |
| 4,815,478 | 3/1989 | Buchbinder et al. . |
| 4,841,976 | 6/1989 | Pakcard et al. . |
| 4,848,342 | 7/1989 | Kaltenbach . |
| 5,065,769 | 11/1991 | Toledo . |
| 5,067,489 | 11/1991 | Lind . |
| 5,069,217 | 12/1991 | Fleischhacker, Jr. . |
| 5,069,674 | 12/1991 | Fearnot et al. . |
| 5,129,890 | 7/1992 | Bates et al. . |
| 5,147,317 | 9/1992 | Shank et al. . |
| 5,178,158 | 1/1993 | de Toledo . |
| 5,213,111 | 5/1993 | Cook et al. . |
| 5,217,026 | 6/1993 | Stoy et al. . |
| 5,228,453 | 7/1993 | Sepetka . |
| 5,241,970 | 9/1993 | Johlin, Jr. et al. . |
| 5,259,393 | 11/1993 | Corso, Jr. et al. . |
| 5,267,574 | 12/1993 | Viera et al. . |
| 5,333,620 | 8/1994 | Moutafis et al. . |
| 5,433,200 | 7/1995 | Fleischhacker, Jr. . |
| 5,443,907 | 8/1995 | Slaikeu et al. . |
| 5,460,187 | 10/1995 | Daigle et al. . |
| 5,514,128 | 5/1996 | Hillsman et al. . |

FOREIGN PATENT DOCUMENTS

| | | |
|---|---|---|
| 0 519 604 A2 | 12/1992 | European Pat. Off. . |
| 0661 073 A1 | 7/1995 | European Pat. Off. . |
| 0 770 404 A1 | 5/1997 | European Pat. Off. . |
| WO 90/01892 | 3/1990 | WIPO . |
| WO 91/00051 | 1/1991 | WIPO . |
| WO 92/13483 | 8/1992 | WIPO . |
| WO 94/10907 | 5/1994 | WIPO . |

*Primary Examiner*—Max Hindenburg
*Attorney, Agent, or Firm*—Henry W. Collins

[57] ABSTRACT

A guidewire having an elongated core including a distal section having a relatively supple portion, a bendable portion, and an enlarged terminal portion, a radiopaque helical member disposed about the bendable portion and structurally interconnecting the terminal portion and the supple portion, and a thin walled flexible sheath tightly surrounding at least a portion of the enlarged terminal section and overlying the bendable portion, the sheath comprised of lubricious material that enhances endwise guidewire movement.

4 Claims, 4 Drawing Sheets

GUIDEWIRE WITH OUTER SHEATH

BACKGROUND OF THE INVENTION

1. Field of the Invention

The present invention relates to guidewires for traversing vessels of vascular systems, and more specifically to guidewires having a radiopaque distal end that bends yet reliably transmits steering torques.

2. Description of the Prior Art

Percutaneous angioplasty is a therapeutic medical procedure that can increase blood flow through a blood vessel. It can sometimes be used as an alternative to coronary by-pass surgery. An elongated guidewire is fed into the patient's vascular system through an incision in the groin. The guidewire tip is guided into position in a coronary artery. A catheter having a deflated balloon near its distal end is fed along the guidewire through the patient's cardiovascular system to a narrowed section of the coronary artery where the angioplasty is to be performed. When properly positioned, the balloon is inflated to compress deposits that have accumulated along the inner wall of the coronary artery to widen the artery lumen and increase blood flow.

The guidewire is steered through the cardiovascular system and its progress is viewed on an x-ray imaging screen. The guidewire tip is advanced through the narrowed coronary artery section in order to position the balloon in the narrowed section. The guidewire tip must be steered through tortuous vessels and/or through junctures of vessels that require tight turns. The tip is bent to facilitate steering the guidewire around tight turns. The proximal guidewire end is twisted about its axis to transmit torque through the guidewire for steering its tip.

SUMMARY OF THE INVENTION

The present invention provides a vascular guidewire constructed for introduction into a patient's vascular system and traversing vessels in the vascular system. The new guidewire comprises an elongated core, a radiopaque coil at the core tip, and a thin walled flexible lubricious sheath forming a smoothly contoured lubricious tip end surface.

The core comprises a body section with a first diametrical extent and a distal section extending from the body section. The distal section comprises a first distal portion whose diametrical extent is diminished proceeding away from the body section, a second distal portion forming an enlarged distal section terminus, and a third distal portion between the first distal portion and the second distal portion. The third distal portion is relatively easily deformable compared to the first and second distal portions and is bent so that the first and second distal portions define an obtuse included angle that facilitates guiding the distal section.

The radiopaque coil is disposed about the third distal portion. The coil has a first end anchored to the first distal portion and a second end anchored to the second distal portion. The coil is defined at least in part by convolutions that are resiliently deflected in the region of the third distal portion bend.

The sheath has a first end disposed about and surrounding at least part of the enlarged terminal distal portion, a second end disposed about and engaging the first distal portion, and an intermediate sheath body disposed about and engaging the coil. The first end resiliently hugs the enlarged terminal portion to form a smoothly contoured lubricious distal section end surface that moves in low friction contact with tissue in a vessel being traversed. The second sheath end is located proximally from the location where the second coil end is anchored to the distal core section. The intermediate sheath body resiliently engages the coil and flexes at the region of the third distal portion bend.

DESCRIPTION OF A PREFERRED EMBODIMENT

Figure 1:
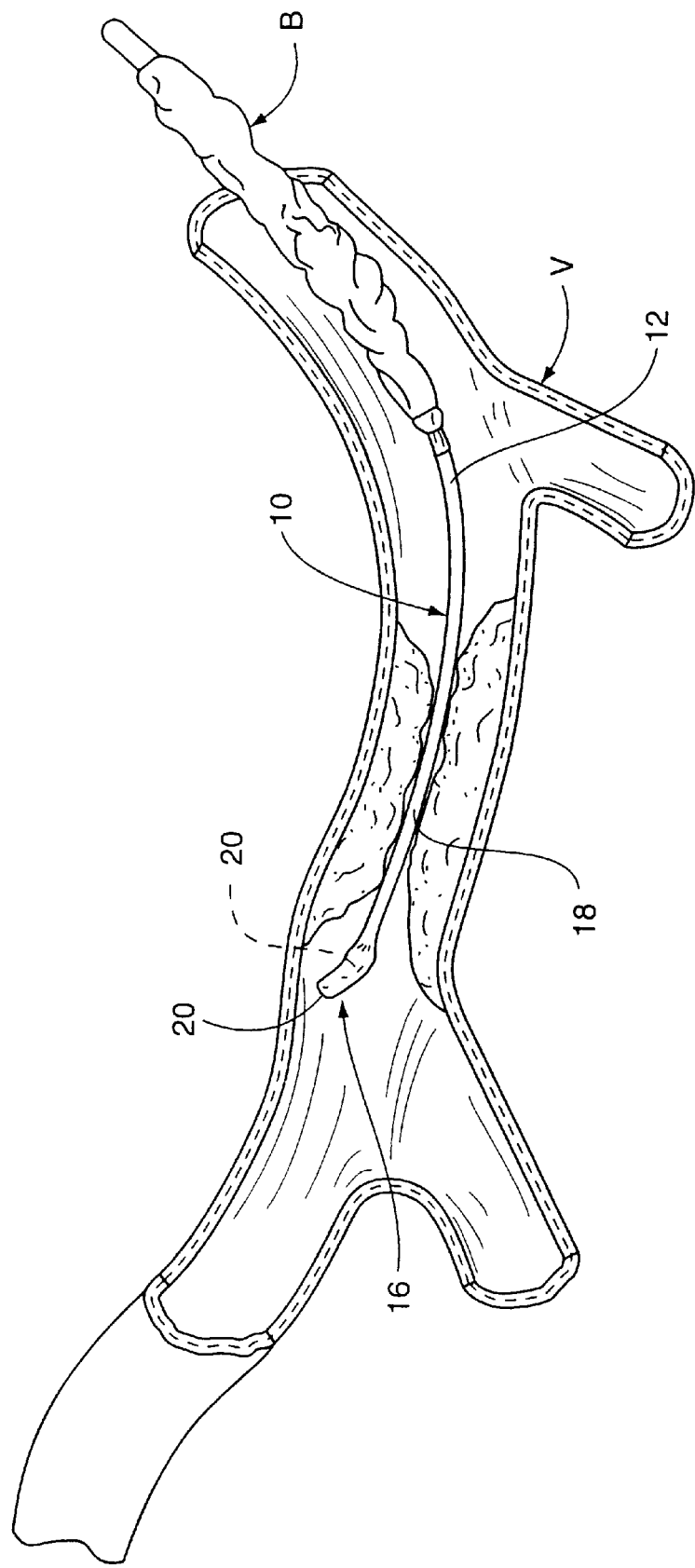
FIG. 1 is a diagrammatic view showing a blood vessel partly occluded by tissue deposited along an inner wall with part of a flexible guidewire embodying the invention disposed in the blood vessel.
Figure 2:
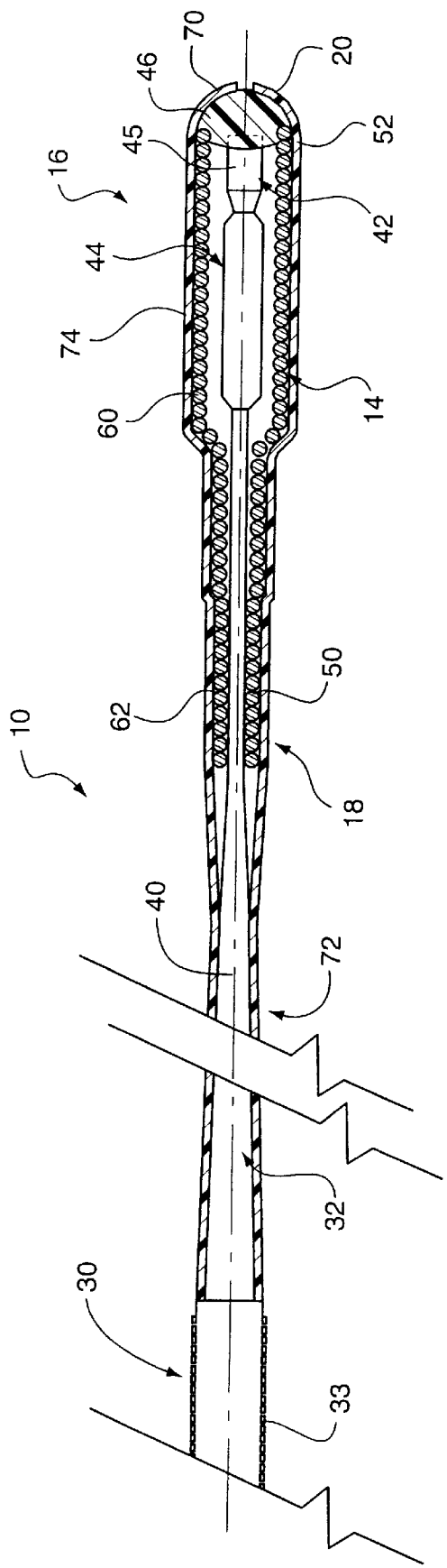
FIG. 2 is a fragmentary elevational view of a flexible guidewire constructed according to the invention.

Turning now to the drawings, FIGS. 1 and 2 illustrate a long, flexible guidewire 10 that is so constructed and arranged that it can be introduced into a patient's cardiovascular system percutaneously and guided to a remote location by the use of x-ray imaging equipment. A distal end of the guidewire is shown in FIG. 1 as having passed through a region in a blood vessel V that is partially occluded with tissue deposited on the vessel wall to the extent that blood flow through the vessel V is unduly restricted. The guidewire 10 is sufficiently long to traverse the vessels from an incision in the patient's groin area to an occluded blood vessel, such as a coronary artery, and has a radiopaque tip to enable x-ray imaging. As the guidewire 10 traverses the often tortuous path through the patient's vascular system to the occluded vessel, it is steered by the physician conducting the procedure.

FIG. 1 illustrates the guidewire 10 routing a balloon catheter B to the occlusion so that an angioplasty may be performed. The balloon catheter is tubular and inserted over the proximal end (not illustrated) of the guidewire. The balloon catheter is advanced along the guidewire until the balloon is positioned in the occlusion. The balloon is inflated with fluid introduced through the catheter for reopening the occluded vessel. The guidewire 10 must be moved through the occlusion to enable the balloon to be positioned properly for the procedure.

The guidewire 10 comprises an elongated core 12, a radiopaque coil 14 at the core tip 16, and a thin walled flexible lubricious sheath 18 covering the coil 14 and forming a smoothly contoured lubricious tip end surface 20.

The core 12 comprises a body section 30 with a first diametrical extent and a distal section 32 extending from the body section 30. In a preferred embodiment the core has a length of 175 cm. (approximately 69 inches). The proximal core butt end (not shown) is formed with suitable wrench flats that are engageable by an appropriate tool for applying steering torque to the core. Steering torque is transmitted through the core to the core tip 16.

Referring to FIG. 2, the body section 30 is formed by a thin wire-like member having a uniform diametrical extent from the butt end to the distal section 32. The outer surface of the body section 30 is lubricious so that it easily slides along the vessel walls. The preferred guidewire body section 30 has a coating 33 of polytetrafluoroethylene applied by spraying. In the preferred and illustrated embodiment of the invention the section 30 is cylindrical and formed from a metallic material, such as stainless steel. Other suitable materials can be used. The illustrated body section 30 extends well over half the length of the guidewire (i.e. about 60 in), is formed by a grinding operation and has a constant diameter in the range 0.009–0.038 inches.

The distal section 32 projects from the body 30 and forms a guidewire end region of increased flexibility compared to the body 30. The section 32 comprises a first distal portion 40 whose diametrical extent is diminished proceeding away from the body section, a second distal portion 42 forming an enlarged distal section terminus, and a third distal portion 44 between the first distal portion 40 and the second distal portion 42.

The first distal portion 40 is illustrated as tapered with a diametrical extent that gradually diminishes proceeding away from the juncture between the body section 30 and the distal portion 40. The illustrated distal portion 40 is cylindric and generally conically tapered. The preferred distal portion 40 is formed from metal—such as stainless steel—and ground to its final configuration. Other suitable materials could be employed and the diametrical extent of the distal portion 40 can be diminished in a stepwise fashion if convenient or desirable. In the preferred guidewire, the distal portion 40 is formed by a succession of tapered wire segments, only one of which is illustrated.

The second distal portion 42 comprises a wire-like segment 45 extending from the third distal portion 44 and a guidewire terminus 46. The terminus 45 has a diametrical extent that is larger than that of the segment 45 and the adjacent end of the first distal portion 40. The coil 14 is anchored to the terminus 46. The sheath 18 at least partially surrounds the terminus. The preferred and illustrated terminus 46 has a smooth, continuous exterior forming a guidewire leading surface that is not abrasive or otherwise likely to damage the sheath or any delicate tissue it may contact during guidewire use. The illustrated terminus is formed by a ball weld—created by laser or plasma welding—that is bonded to the segment 45 and to the coil 14. The illustrated segment 45 is a cylinder having an enlarged diameter compared to the end of the distal portion 40.

The third distal portion 44 is relatively easily deformable compared to the first and second distal portions 40, 42 and is bent, in use (see FIG. 1), so that the first and second distal portions define an obtuse included angle that facilitates steering the guidewire. The distal portion 44 is preferably formed by stamping and upsetting a cylindrical section of the distal section 132 to flatten it and produce a thin ribbon-like portion of the distal section between the portions 40, 42. The portion 44 thus defines a thin rectangular cross sectional shape that is relatively easy to bend in the direction of its thickness yet more stiffly resists bending in the direction of its width. The portion 44 is normally bent during manufacture so that the portions 40, 42 define an included angle of 35°. The portion 44 is easily bent by the physician to adjust it to whatever included angle is desired, usually some angle between 25° and 45°.

The radiopaque coil 14 is disposed about the third distal portion 44. The coil has a first end 50 anchored to the first distal portion 40 and a second end 52 anchored to the second distal portion 42. The coil 14 is defined at least in part by convolutions 60 that surround the distal portion 44 and are resiliently deflected in the region of the third distal potion bend. The illustrated coil end 50 is formed by convolutions 62 that surround and tightly grip the distal portion 40 near its juncture with the distal portion 44. In the preferred embodiment of the invention the convolutions 62 are bonded to the distal portion 40 so that the coil end 50 is securely affixed to the core 12. In the illustrated embodiment of the invention a body of bonding material is disposed between the convolutions 62 and the distal portion. The preferred embodiment employs a nylon plastic material that is flowed around and between the convolutions and the core wire and then cured in place to bond the two together.

The convolutions 62 are illustrated as tapering to conform to the shape of the distal portion 40 and then tapering to an enlarged coil diameter to merge into the convolutions 60. The convolutions 62 are illustrated as having a rectangular cross sectional shape where they extend along the distal portion 40.

The convolutions 60 closely surround the distal portion 44 and end at the terminus 46. The illustrated convolutions 60 are wound so that, before the distal portion 44 is bent, adjacent coil turns are separated slightly. This permits the distal portion 44 to bend while minimizing stress in it and the coil. The illustrated convolutions 60 are formed of circular cross section wire and form a straight cylindrical helix before the distal portion 44 is bent.

The coil end 52 is securely bonded to the terminus 46 in the preferred embodiment of the invention. Preferably the end 52 is welded to the ball weld so that the coil 14 structurally interconnects the distal portions 40, 42. The coil 14 is fabricated from a material that is highly radiopaque, such as platinum wire having a diameter of 0.002 to 0.003 inches.

The sheath 18 is a thin walled lubricious turbular member that resiliently embraces the guidewire tip 16, the coil 14, and at least the end region of the distal portion 40 adjacent the coil. The sheath 18 has a first end 70 disposed about and surrounding at least part of the enlarged terminus 46, a second end 72 disposed about and engaging the first distal portion 42, and an intermediate sheath body 74 disposed about and engaging the coil 14. The sheath end 70 resiliently hugs the terminus 46 to form the smoothly contoured lubricious distal section end surface 20 that moves in low friction contact with tissue in a vessel being traversed. The second sheath end 72 is located proximally from the location where the second coil end 52 is anchored to the distal section 40. The intermediate sheath body 74 resiliently engages the coil 14 and flexes freely at the region of the third distal portion bend.

Figure 3:
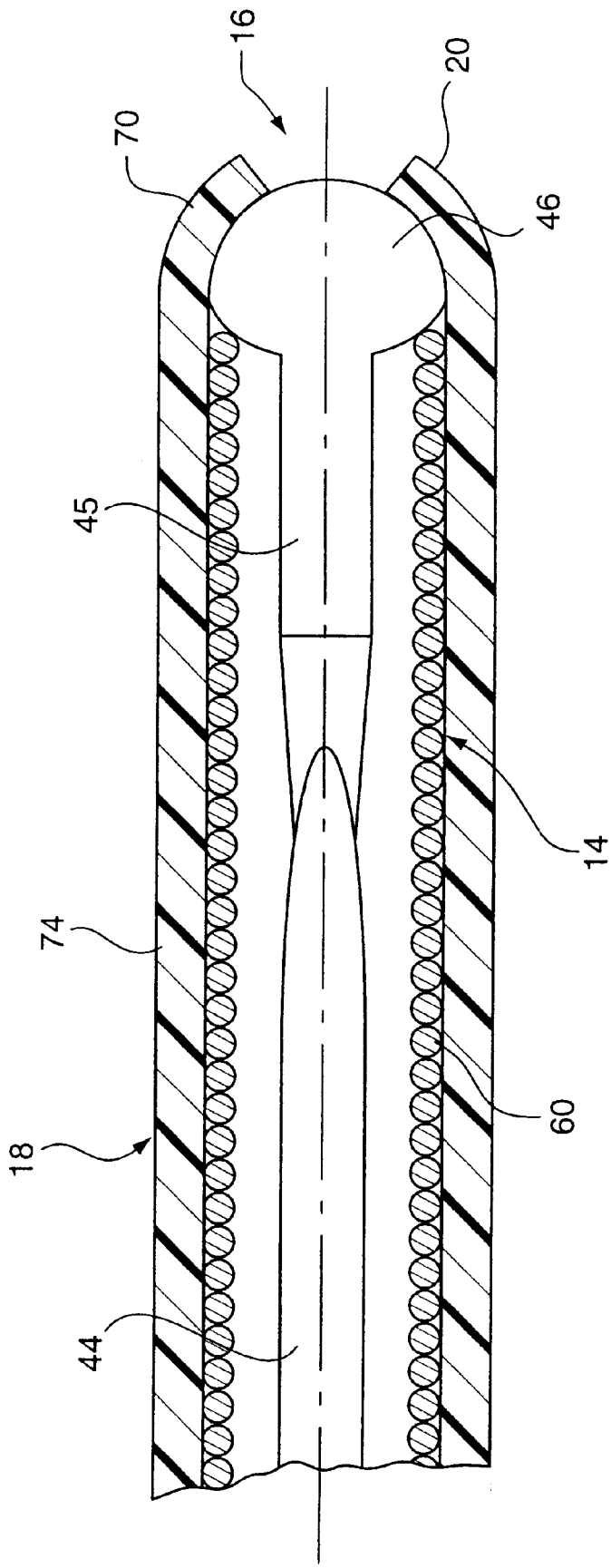
FIG. 3 is an enlarged view seen approximately from the plane indicated by the line 3—3 of FIG. 2; and, FIG. 4 is a view, similar to FIG. 3, of a modification of the guidewire of FIGS. 2 and 3.

In the preferred embodiment of the invention the sheath 18 is an open ended tube formed from polytetrafluoroethylene that is heat shrunk into resilient engagement with the guidewire. As best illustrated in FIG. 3, the sheath 18 is shrunk into place about the ball weld with the sheath end 70 covering substantially all of the ball weld outer surface. The preferred and illustrated sheath end 72 extends continuously to the juncture between the core sections 30, 32.

Figure 4:
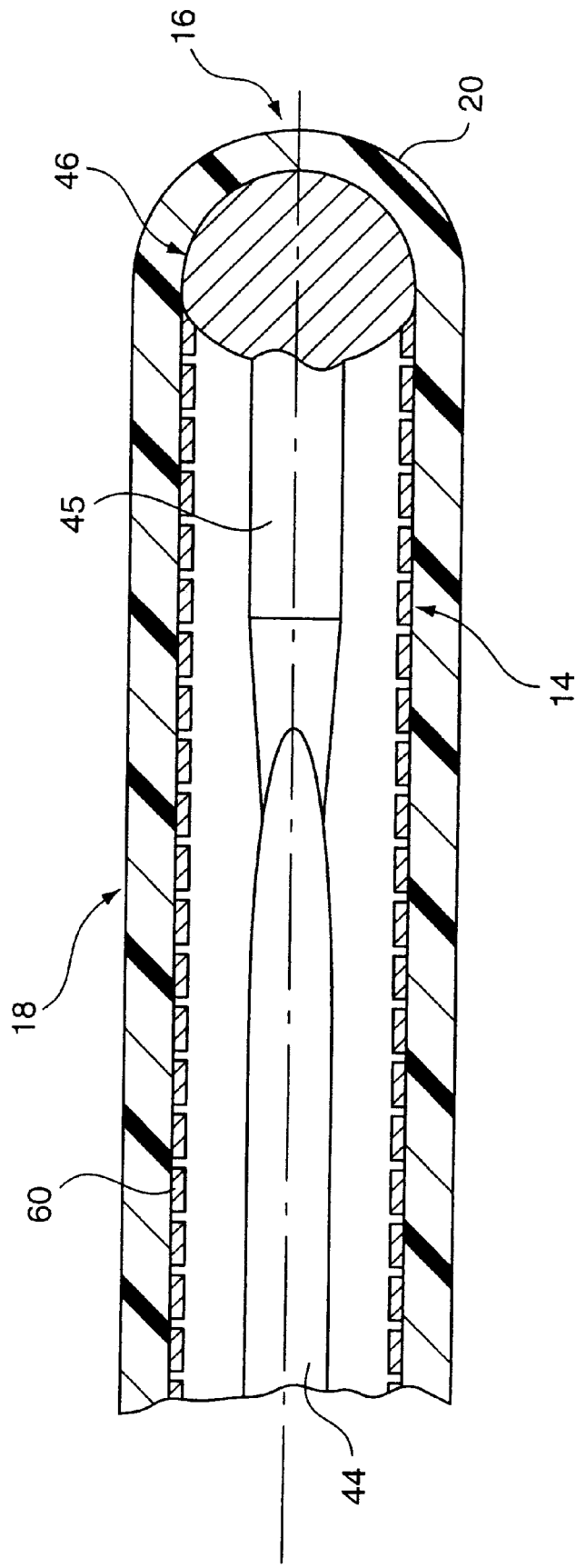

FIG. 4 of the drawings illustrates an alternative construction in which the sheath 18 is formed from a closed end, sock-like tube and the coil 14 is formed from wire having a rectangular cross sectional shape. The tube is formed from heat shrinkable polytetrafluoroethylene film that completely covers, and snugly engages, the ball weld surface. The tube open end (not shown) of the preferred embodiment of the invention extends to the juncture between the core sections 30, 32. The continuous tube end assures that a lubricious guidewire end surface 70 is provided for advancing through the vascular system.

The rectangular cross section wire forming the coil provides a stiffer, stronger support for the guidewire end as well as enabling the guidewire end to be formed with a smaller overall diametrical extent than it would have if the coil were made of round cross sectional wire.

While two embodiments of a guidewire constructed according to the invention have been illustrated and described in detail, the invention is not to be considered limited to the precise constructions disclosed. For example, while a coil 14 is illustrated as having a stepped outer diameter with the largest diametrical extent at the guidewire tip, the coil 14 could be constructed from a helix having a constant diametrical extent. Various adaptations, modifications, and uses of the invention may occur to those skilled in the business to which the invention relates. The intention is to cover all such adaptions, modifications, and uses that fall within the sprint or scope of the attached claims.

That which is claimed is:

1. A vascular guidewire constructed for introduction into a patient's vascular system and traversing vessels in the vascular system comprising:

a) an elongated core having a body section with a first diametrical extent and a distal section extending from said body section, said distal section comprising a first distal portion whose diametrical extent is diminished proceeding away from said body section, a second distal portion forming an enlarged distal section terminus, and a third distal portion between the first distal portion and the second distal portion, said third distal portion relatively easily deformable compared to said first and second distal portions;

b) a radiopaque coil disposed about said first, second and third distal portions, said coil having a first end anchored to said first distal portion and a second end anchored to said second distal portion; and, c) a thin walled sheath comprised of polytetrafluroethylene material heat shrunk about said first, second and third distal portions, a first end of said heat shrunk sheath resiliently hugging said enlarged terminal portion to form a smoothly contoured lubricious distal section end surface that moves in low friction contact with tissue in a vessel being traversed, and a second end of the sheath is anchored to said first distal core section.

2. The guidewire of claim 1, wherein said third distal portion is defined, at least in part, by a relatively thin, generally rectangular cross sectional shape.

3. The guidewire of claim 2, wherein the radiopaque coil is formed at least in part by a helix having closely spaced convolutions.

4. The guidewire claimed in claim 3, wherein said second coil end has a larger diametrical extent than said first coil end.

* * * * *